United States Patent
Jones et al.

(10) Patent No.: US 8,060,696 B2
(45) Date of Patent: Nov. 15, 2011

(54) POSITRON EMISSION TOMOGRAPHY EVENT STREAM BUFFERING

(75) Inventors: William F. Jones, Knoxville, TN (US);
John E. Breeding, Knoxville, TN (US);
Johnny H. Reed, Clinton, TN (US);
Jimmy Everman, Maryville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 425 days.

(21) Appl. No.: 12/437,714

(22) Filed: May 8, 2009

(65) Prior Publication Data
US 2009/0313430 A1    Dec. 17, 2009

Related U.S. Application Data (63) Continuation-in-part of application No. 12/110,485, filed on Apr. 28, 2008.

(60) Provisional application No. 61/126,877, filed on May 8, 2008, provisional application No. 60/914,420, filed on Apr. 27, 2007, provisional application No. 60/984,062, filed on Oct. 31, 2007.

(51) Int. Cl.
*G06F 12/16* (2006.01)
(52) U.S. Cl. .................................. 711/114; 711/110
(58) Field of Classification Search ............ 711/114, 711/110
See application file for complete search history.

(56) References Cited

U.S. PATENT DOCUMENTS

| | | | |
|---|---|---|---|
| 6,907,099 B2 | 6/2005 | Kling et al. | |
| 7,155,569 B2 * | 12/2006 | Johnson et al. | 711/114 |
| 7,287,134 B2 * | 10/2007 | Miller et al. | 711/158 |
| 7,302,520 B2 * | 11/2007 | Kazar et al. | 711/114 |
| 7,302,522 B2 * | 11/2007 | Khan et al. | 711/114 |
| 7,310,703 B2 * | 12/2007 | Frolund et al. | 711/114 |
| 7,313,719 B1 * | 12/2007 | Elahee | 714/6.11 |
| 7,353,336 B2 * | 4/2008 | Gaither | 711/122 |
| 7,363,426 B2 * | 4/2008 | Ahmadian et al. | 711/114 |
| 7,370,145 B2 * | 5/2008 | Ikeuchi et al. | 711/113 |
| 7,370,175 B2 * | 5/2008 | Zimmer et al. | 711/114 |
| 2004/0141661 A1 | 7/2004 | Hanna et al. | |
| 2007/0106537 A1 | 5/2007 | Moore | |
| 2008/0168195 A1 | 7/2008 | Feihl | |

* cited by examiner

*Primary Examiner* — Michael Tran
(74) *Attorney, Agent, or Firm* — Peter L. Kendall (57) ABSTRACT

PET system including array, data processing, and data acquisition. Data acquisition includes one-to-N channel write striping, N-to-one channel read unstriping, N data storage elements, and control logic. Control logic allocates (statically or dynamically) write/read access to data storage elements. Dynamic allocation can be conditional, e.g., that data storage elements be available to receive all input data from array. Embodiments include an input buffer where the condition is determined dynamically based on capacity of the input buffer to temporarily preserve all input data supplied during periods data storage element unavailability. Communication between array and data acquisition can be Fibre Channel simplex implementing only FC-0, FC-1. Data storage elements have data handling bandwidth equal to or greater than (data output rate /N) plus (data input rate/N). Control logic, write striping, read unstriping can be implemented in FPGA. Data storage elements can form a Redundant Array of Independent Disks, e.g., RAID 0.

30 Claims, 6 Drawing Sheets

POSITRON EMISSION TOMOGRAPHY EVENT STREAM BUFFERING

CROSS REFERENCE TO RELATED APPLICATIONS

The present application claims the priority benefit of pending U.S. Provisional Patent Application No. 61/126,877 titled "A Digital Architecture for Routinely Storing and Buffering the Entire 64-Bit Event Stream at Maximum Bandwidth for Every Acquisition in Clinical RealTime 3-D PET: Embedding a 400 Mbyte/sec SATA RAID 0 Using a Set of Four Solid-State Drives," filed May 8, 2008 (the "Provisional Application"). The complete disclosure of the Provisional Application is hereby incorporated herein by reference in its entirety.

The present application claims the priority benefit of pending U.S. patent application Ser. No. 12/110,485 titled "System For Simulating PET Gantry," filed Apr. 28, 2008 and claiming priority to U.S. Provisional Patent Application No. 60/984,062, filed Oct. 31, 2007 and U.S. Provisional Patent Application No. 60/914,420, filed Apr. 27, 2007. The complete disclosure of these applications is hereby incorporated herein by reference in their entirety.

FIELD OF THE TECHNOLOGY

The technology disclosed herein relates to data acquisition in positron emission tomography (PET) systems.

BACKGROUND

Data acquisition in high-performance clinical 3-D PET has for years been burdened with an unfortunate trade-off. From even the early days of PET, the user has been forced to choose between convenient real-time processing, e.g., on-line rebinning and histogramming, and the collection of the raw information-rich detector-pair list-mode data, e.g., typically in the form of multiple 64-bit packets describing coincident events. Typically, the latter choice also limited the maximum count rate supported without data loss. Systems that could perform both functions at the same time were usually too costly and too complex.

Existing PET data acquisition architecture requires that the on-line processing (LOR-to-bin rebinning and histogramming) be designed with throughput which is no less than the maximum event rate generated by the PET detector array. If the on-line processing throughput fell short, the result was loss of precious PET data during high-count-rate intervals. Achieving extra on-line processing throughput was often expensive if even achievable. In addition, performing on-line processing simultaneous with uncompromising list-mode data acquisitions was difficult if not impossible to achieve.

SUMMARY

A (PET) system including a PET array, a PET data processing assembly, and a PET data acquisition assembly. The data acquisition assembly includes a one-to-N channel write striping assembly in read communication with the PET array, an N-to-one channel read unstriping assembly in write communication with the PET data processing assembly, and a plurality, N, of data storage elements. Each data storage element is in read communication with one of the N channels of the write striping assembly, and in write communication with one of the N channels of the read unstriping assembly. The data acquisition assembly also includes control logic. The control logic allocates write and read access to the N data storage elements. In some embodiments, allocation is static, e.g., one half the data handling capacity of the data storage elements is allocated to read access and one half to write access. In some embodiments the control logic allocates read access to the N data storage elements only on a condition that the N data storage elements be available to receive all input data from the PET array. In some embodiments, the acquisition assembly includes an input buffer. In those embodiments the condition is determined dynamically at least in part as a function of the capacity of the input buffer to preserve all PET input data supplied to the PET data acquisition assembly by the PET array. In some embodiments, the data communication between the PET array and the PET data acquisition assembly is Fibre Channel simplex implementing only the FC-0 and FC-1 layers. In some embodiments, each of the plurality of N data storage elements is characterized by a data handling bandwidth equal to or greater than the (data output rate/N) plus the (data input rate/N). In some embodiments, control logic assembly, write striping assembly, and read unstriping assembly are implemented in a Field Programmable Gate Array (FPGA). In some embodiments, the data storage elements form a Redundant Array of Independent Disks (RAID), e.g., a RAID 0.

DETAILED DESCRIPTION

Reference will now be made in detail to embodiments of the technology. Each example is provided by way of explanation of the technology only, not as a limitation of the technology. It will be apparent to those skilled in the art that various modifications and variations can be made in the present technology without departing from the scope or spirit of the technology. For instance, features described as part of one embodiment can be used on another embodiment to yield a still further embodiment. Thus, it is intended that the present technology cover such modifications and variations that come within the scope of the technology.

A stream buffer data acquisition technology for PET improves performance in high-count-rate (e.g. Rubidium-82) clinical 3-D PET systems. This technology improves PET, at least in part, by removing several long-running limitations found in current data acquisition architectures. Stream buffering provides the opportunity for storage of the entire, raw 64-bit PET coincidence event stream. In addition, buffering benefits downstream processes, e.g. Line of Response (LOR)-to-bin rebinning and histogramming; processes that remain important to an effective clinical environment.

Some embodiments of the technology make use of high-performance solid-state drives (SSDs) to form a single, very-high-speed (e.g., 400 MB/s) Redundant Array of Independent Disks (RAID) buffer for coincidence event data. For reference, many SSDs make use of NAND flash chips for storage instead of rotating media. In some embodiments SRAM or DRAM, instead of or in combination with flash memory, e.g., a Random Access Memory (RAM) drive, can be used. In other embodiments, phase change or resistor memory can be used to implement the RAID. Existing SSDs readily exceed 100 MB/s for read/write throughput. In embodiments of the present technology, a set of Serial Advanced Technology Attachment (SATA) SSDs are configured as an embedded RAID under the direct control of an FPGA to store raw PET array data. Though the present technology can be implemented using various versions of RAID, in particular embodiments described herein, 4 SATA SSDs are configured as a 64 GB RAID 0; and are variously referred to as "RAID" and "RAID 0." Technology such as phase change memory (Samsung, Numonyx, etc.) can be employed as an alternative to SSD and RAID in this application. With a bank of fast, nonvolatile phase change memory chips locally installed in a stream buffer, similar benefits to clinical PET data acquisition may also be realized.

A Field Programmable Gate Array (FPGA) implements a striping RAID controller expected in a RAID 0. A four-channel RAID implemented with current state-of-the-practice hardware (see below) offers a sustainable, aggregate bandwidth of at least 400 MB/s. The stream buffer PET technology implements high-speed, time-shared write/read access into/from this RAID. With both read and write accesses each available for sustainable portions of the aggregate bandwidth, e.g. 200 MB/s throughput for each of read/write in 400 MB/s systems allocating read/write access equally, stream buffering improves PET data acquisition in several ways. Once the PET event stream is delivered to the FPGA that controls the embedded RAID, e.g. via 2 Gbps Fibre Channel, none of the event stream data need be lost because of insufficient bandwidth. A non-volatile copy of the raw 64-bit PET event stream data can be preserved for post-acquisition processing whether on-line downstream processing is selected or not. The RAID output proceeds, under the control of the RAID controller, only at the available downstream throughput rate, i.e. mitigating, if not eliminating, the criticality of higher downstream throughput needed to prevent event loss. In some embodiments, the controller prioritizes write transactions at the expense of read transactions to lower the risk of losing the raw PET array data.

On-line cardiac and respiratory gating also benefit. For example, more complex processing for gating can occur concurrent with the acquisition. With the stream buffer technology, effective prospective gating involving both cardiac and respiratory triggers and/or waveforms with real-time or near real-time gating decisions spanning multiple cardiac and/or respiratory cycles, while also serving the needs of dynamic gating along with continuous bed motion performed concurrent with the acquisition, becomes a possibility for the first time in clinical PET.

Recently, the computer industry has begun to offer a growing selection of solid state drives (SSD), i.e., drives using only memory chips (e.g. NAND flash) offering improved speed and reliability over the more traditional rotating disk drives. Recent news releases from various SSD developers (e.g. Samsung, Micron, and Intel) promise to quickly make solid-state drive systems ever more cost effective and faster.

Figure 1:
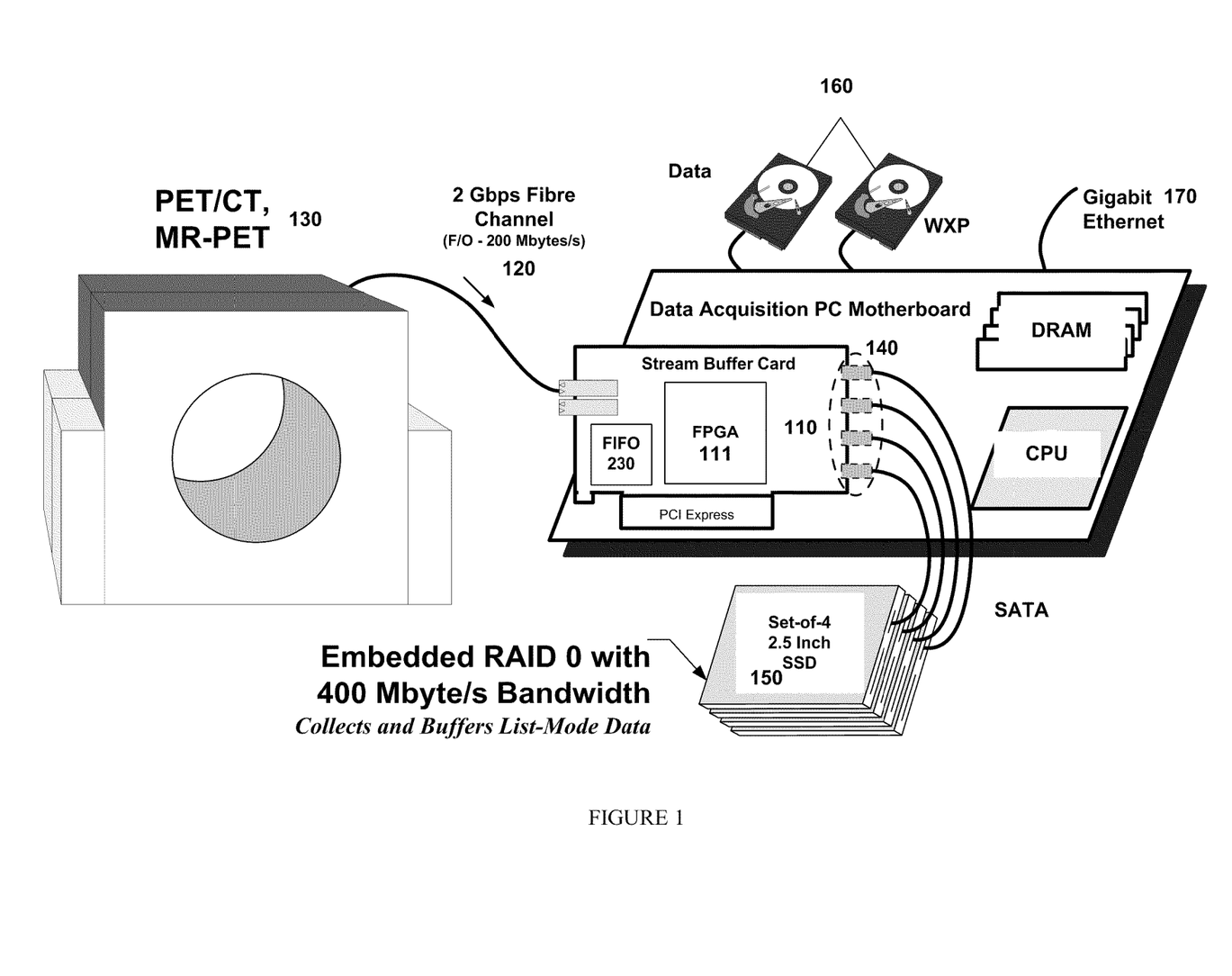
FIG. 1 is an illustration of an exemplary embodiment of the technology within a PET data acquisition architecture.

Referring to FIG. 1, an exemplary embodiment of the technology within a PET data acquisition architecture is shown. A stream buffer card 110 is connected via Fibre Channel 120 to the PET detector array 130; and via a multipoint SATA interface 140 to a RAID 150. In some embodiments, the FC F/O interface 120 is dedicated to bringing PET array 130 data, e.g., not previously stored in nonvolatile media data, to the stream buffer; it is not used to provide a RAID-hosting link between the RAID controller (described below) and another processor. The stream buffer card 110 and RAID 150 allow the 64-bit detector-pair list-mode data set from the PET array 130 to be stored during data acquisition. The high bandwidth of the RAID allows this list-mode data to be read during the acquisition, via time sharing of the 4 SATA interfaces 140. With current SSD product offerings, an array of four SATA SSDs, when configured as a RAID 0 150 and driven from a FPGA 111 as in FIG. 1, supports a combined read/write bandwidth of 400 MB/s. A portion of this bandwidth (e.g., 200 MB/s of aggregate throughput) can be allocated to writing 64-bit detector-pair list-mode data sequentially as generated in real time by the PET detector array 130. The remaining portion of this bandwidth is dedicated to reading data from the RAID 150 for purposes such as long term storage, e.g., on data stores 160 of the data acquisition platform or off-board via network connections 170, and further down-stream processing, e.g., processing such as rebinning and histogramming. Allocation of RAID read/write bandwidth can be dynamic and under the control of the FPGA in communication with other system elements through a channel, e.g., PC-Express interface, other than the FC F/O carrying the PET array data. With such read/write time sharing of the RAID 150, the stream buffer addresses the unfortunate tradeoff mentioned above. With this technology in place, the user still will enjoy real-time generation of projection data, e.g., data that is available at the end of each acquisition. Further a complete non-volatile copy of the raw 64-bit list-mode data is also preserved for post-acquisition analysis. The list-mode data set can be preserved for each and every data acquisition whether on-line rebinning and histogramming are selected as part of the data acquisition or not. The stream buffer decouples collection of the raw data as generated by the PET array from concurrent downstream processing.

Figure 2:
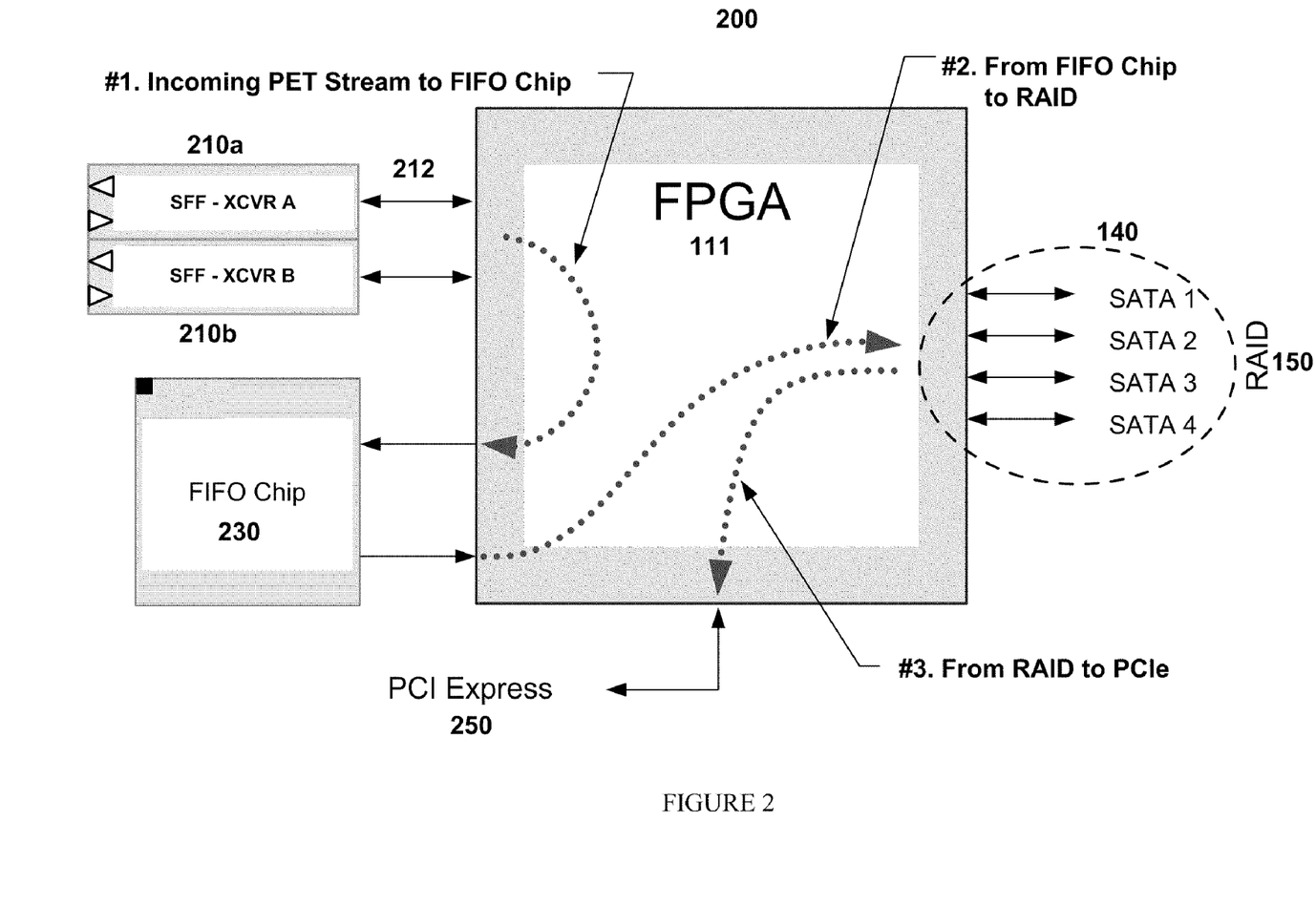
FIG. 2 is a block diagram for an exemplary stream buffer.

FIG. 2 presents a block diagram for embodiments of the stream buffer 200. Fibre Channel (FC) fiber-optic (F/O) transceivers 210a and 210b (e.g., Stratos SLC-25-8-X-R6 for 2 Gbps or Finisar FTLF8524E2xNL for faster) deliver a 64-bit PET detector-pair packet stream 212. One transceiver is used to receive the PET array data stream. This input stream is loaded (via an FPGA 111, e.g., a Xilinx Virtex 5™) into the FIFO chip 230 (e.g., IDT IDT72T36135M). Local buffering on the FIFO chip 230 preserves PET array 130 data during periods in which the RAID 150 is unavailable for writing, e.g., during a read of the RAID, during periods in which the SSDs are unresponsive (e.g., the idle phase of the SSDs). The FIFO chip 230 output is written to the RAID 150 via the FPGA 111 through the SATA interface 140. The data read from the RAID 150 is output either via the second F/O transceiver 210b (preferably duplex to support flow control), e.g., to some other card for more hardware-based on-line processing; or via the PCI-E interface 250, e.g., to the motherboard of a computer acting as a platform for the acquisition system. The PCI-E interface 250 is used to provide command, status, control, and I/O for the stream buffer, e.g., for application code executing elsewhere in the system, and for high speed read/write DMA. Two small form factor (SFF) Fibre Channel fiber-optic transceivers 210a, 210b, are shown at upper left. At lower left is a high-capacity FIFO chip 230. The PCI Express interface 250 is depicted at the bottom. The 4-channel SATA RAID interface 140 is shown at right. Note stream buffer FPGA 111 at the center. In some embodiments the FPGA, FIFO chip, F/C FO transceivers, PCI Express interface, and SATA interface are embodied in a printed circuit board assembly compatible with the form factor of the target hardware platform, e.g., a PC.

Figure 3:
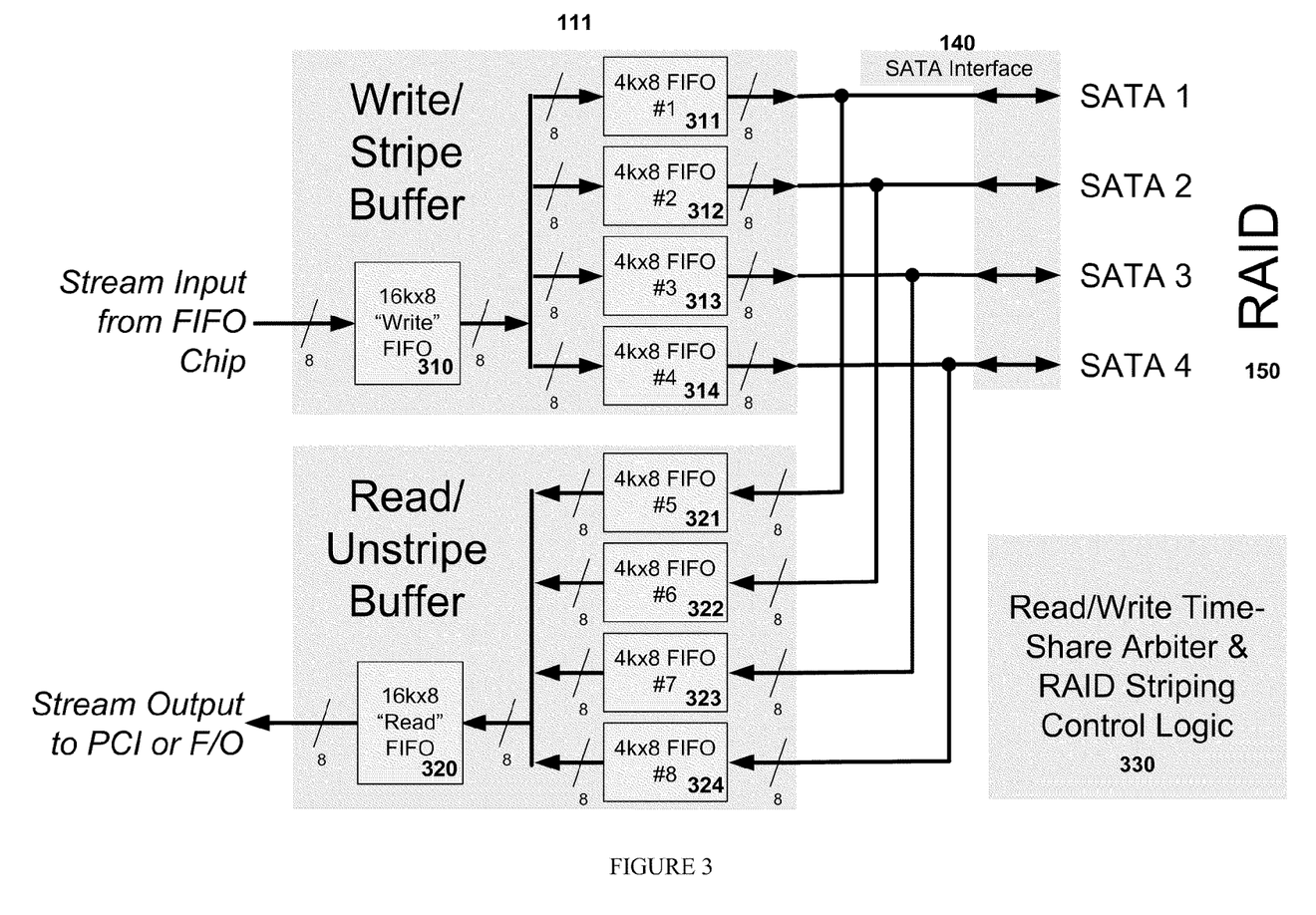
FIG. 3 is a block diagram of an FPGA-resident Redundant Array of Independent Disks (RAID) striping control in a stream buffer.

FIG. 3 is a block diagram illustrating the structure and operation of the FPGA 111. FPGA-resident FIFOs 310, 320 buffer to facilitate write striping and read unstriping at aggregate rates at least as great as the input and output rates of the acquisition system. During write-to-RAID phase, the write/stripe buffer 310 delivers input data via the SATA interfaces 140 to the four physical devices that make up the RAID 150 via FIFO#1-FIFO#4 311-314. Similarly, during read-from-RAID phase, the read/unstripe buffer 320 establishes a read state with the four physical devices that make up the RAID 150 across all four channels of the SATA interface 140 into FIFO#5-FIFO#8 321-324. The FPGA-resident 4k×8 FIFOs are sized to match the typical 4096-byte page size of the SSD. Control of data flow and the read/write phases is accomplished through a read/write time share arbiter and RAID striping control logic 330 programmed into, e.g., embedded in, the FPGA.

At least one SATA SSD is available today which is more than adequate for this application. The MTRON 16 GB SATA 2.0 MSP-SATA 7525016 SSD is in the popular "2.5 inch" form factor. The MTRON SSD offers 120 MB/s write speed and 130 MB/s read speed with an average random access time of 0.1 ms. Given its Input/Output Operations Per Second (IOPS) (random read) of 19,000, write endurance of greater than 140 years at 50 GB write/day, and 2008 price of $479, it can serve well as the RAID 150 in a PET stream buffer. A 64 GB list-mode capacity (built from a set of four 16 GB SSD) is adequate for most of today's PET applications. Even so, higher storage capacities with this same, expected high level of throughput are readily available from this same vendor; albeit, at a higher cost. More recently, the Intel X25-E SSD with 32 GB storage capacity has come available at a similar cost and seems to possess even higher levels of throughput performance.

In some embodiments, the RAID 150 remains unformatted with only the raw, striped file volume to support read/write transactions. Higher levels of RAID sophistication, such as formally formatted file volumes and/or full accessibility as a Windows drive, are characteristic of additional embodiments of the technology. Similarly, wear leveling, a feature of NAND-flash-chip SSD applications is implemented in some embodiments. Even with wear leveling disabled for PET list-mode storage in clinical use, e.g., about twenty (20) studies per day, the SSDs are expected to remain functional for several decades as indicated by the write endurance of the MTRON device.

In embodiments of the technology, write striping functions so that an arriving sequence of data is automatically broken up into channels, e.g., quadrants where there are four SATA channels 140 feeding the RAID 150, as part of the write process. The embodiments disclosed in the Figures use a 4 k-byte FIFO buffer, e.g., 311-314, 321-324, for each channel. Each of the four SATA interfaces handles only one of the four unique quadrants of data. As an example of write striping during a write phase of RAID access, a stream of 32 kB arrives into the stream buffer via the FC interface 120, 210. This arriving stream is loaded into the FIFO Chip 230 via the FPGA 111. This and most other data movement in this context is under control of the FPGA 111, e.g., logic 330.

Using the letter sequence "ABCDEFGH" to represent this contiguous 32 kB stream. Each letter represents 4 kB with the "A" data arriving first. The data sequence "ABCD" is moved out from the FIFO Chip 230 and into the 16 k×8 Write FIFO 310. For the moment, the sequence "EFGH" still resides within the FIFO Chip 230 but will shortly move into this same 16 k×8 FIFO 310. In part, the role of the FPGA 111 is to load the "A" data into FIFO #1 311 as rapidly as feasible without risking loss of data. Next, in sequence the data represented by "B" through "D" are similarly loaded into FIFOs #2-#4 312-314, respectively. As the data are written to SSD storage, the incrementing file-volume offset used in the SATA write is the same for each of the four SSD file volumes. Concurrent with FIFO#1-FIFO#4 311-314 loading, the FPGA 111 is also seeking to unload these same FIFOs at the rates up to the maximum supported rate via simultaneous write transactions across all four SATA channels 140. As soon as the "D" data is loaded into FIFO #4, the write striping sequence repeats but this time by loading the next arriving "E", "F", "G", and "H" data across FIFOs #1 311, #2 312, #3 313, and #4 314, respectively. At the end of this short write striping sequence, the four SSD (SATA 1 through 4) have each stored the data represented by "AE", "BF", "CG", and "DH", respectively. This means that in each case, the writing of data to an SSD in the RAID 150 is sequential, that is with arriving data write-appended to the growing content within the file volume. Since, in this example, all four SATA channels 140 are kept busy at maximum rates, write striping maximizes the overall write throughput to essentially be four times that of any single SSD.

In similar fashion read unstriping functions so that a previously stored-on-RAID stream of data is automatically reassembled from each of the four quadrants as part of the read process so as to correctly reproduce the original order of data arrival. As an example of read unstriping during a read phase of RAID access, four sets of data totaling 32 kB have been previously stored in the RAID across the four SATA channels via the write striping process described above. As before, a set of eight letters are used to represent this data set with each letter referring to 4 k bytes, "ABCDEFGH," again shown in the order desired after reassembly with "A" first. As a result of the write striping case above, the four SSD drives (SATA channels 1 through 4) of the RAID 150 each contain pairs of 4 k byte data sets which are stored contiguously, i.e., "AE", "BF", "CG", and "DH", respectively. Each letter pair shares the same file-volume offset across all four of the SSD drives. As the read unstriping example begins, the FPGA 111, e.g., logic 330, causes the "A" data to be read via SATA 1 into FIFO #5 321 as fast as feasible without loss of data. Concurrently, the other three SATA channels also read the "B" through "D" data from SATA 2 through 4, loading FIFOs #6-#8 323-324, respectively. Concurrent with that 4-channel SATA read cycle, the FPGA begins to unload FIFOs #5 through #8 in sequence. This FIFO unloading occurs such as to correctly reassemble the "ABCD" stream of data into the lower-left 16 k×8 Read FIFO 330 as shown in FIG. 3. The FPGA is also seeking to actively unload this 16 k×8 FIFO 330 into whatever downstream processing path is selected. Next, the entire read unstriping sequence repeats along similar lines but this time assembling the second half of the stream of data, "EFGH". At the start of this second-half portion of the read unstriping example, each of the SSD in the RAID 150 continues on reading sequentially, e.g., from "A" to "D", from "E" to "H", etc. This entire read unstriping sequence is controlled by the FPGA logic 330 to run no faster than may be effectively handled by the chosen downstream channel; be that into the FC F/O output port or, more typically, into the PCI-Express DMA port. In the case of the PCI DMA port, a "demand-mode" type of DMA transfer ensures a lossless flow of data at the maximum bandwidth available from the PC motherboard. This ensures that none of the stream data is lost in the downstream channel due to overfeeding the channel. As in the write striping phase, read unstriping can maximize the potential of the read throughput to essentially be four times that of any single SSD.

Since the 2 Gbps Fibre Channel input into the stream buffer is limited to approximately 200 MB/s, this RAID 150 has double that bandwidth. This 2× bandwidth allows the FIFO chip 230 to burst with a 400 MB/s output during each sequential write phase. As this FIFO chip 230 recovers data content, a time window is presented in which the write phase may be suspended in favor of the sequential read phase, e.g., under control of the logic 330.

Figure 4:
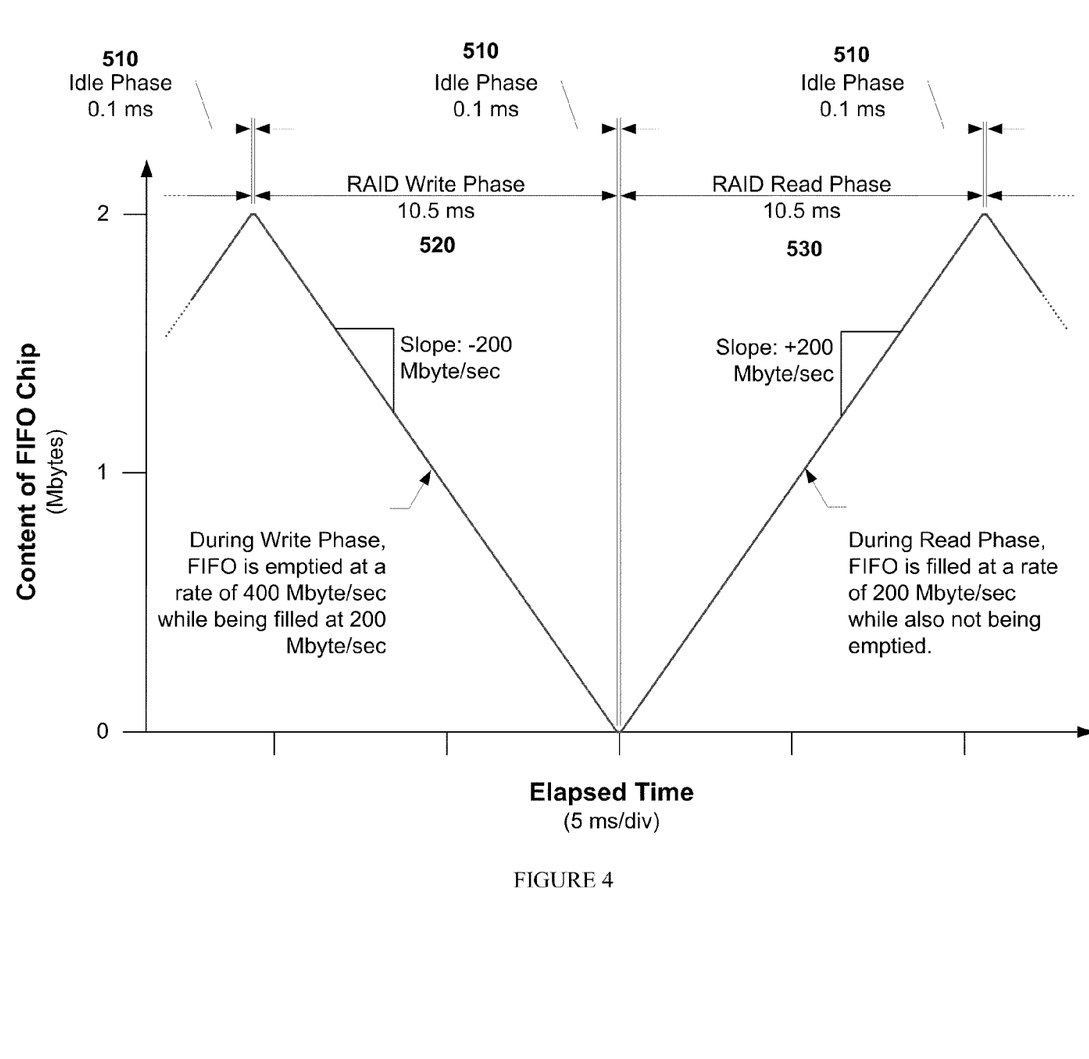
FIG. 4 illustrates data flow volume through a First-In-First-Out (FIFO) chip of a stream buffer.

FIG. 4 illustrates data volume in the FIFO chip 230 over time during write and read phases of the technology. The large FIFO Chip 230 helps ensure that both the write phases and read phases for RAID transactions are long (10.5 ms) compared to the SSD random access time (Idle Phase, 0.1 ms). The write-phase/read-phase cycle as shown may repeat many times (e.g. 30 k) until the arriving data rate slows, the acquisition ends, or the RAID 150 is filled. The size selection of the FIFO Chip 230 is a function of the 0.1 ms random access time of the SSDs that make up the RAID 150. If latencies of longer duration are exhibited by the SSD, larger capacity data buffering is used to ensure data is preserved even during these longest idle periods. Such larger buffering can be implemented with one or more DRAM banks local to the stream buffer. As shown in FIG. 4, with each transition between write and read phases, the SSDs require 0.1 ms of "idle" time 510 due to SSD random access, e.g., a period during which no data is transferred. The FIFO Chip 230 (e.g., with 2 M useful bytes) requires 10.5 ms to fill at the maximum F/O input rate of 200 MB/s—not shown. Each sequential write phase is limited to periods no longer than 10.5 ms 520. In other words, the FIFO Chip empties in 10.5 ms if it is unloaded at 400 MB/s while being loaded via the F/O link at 200 MB/s. This write phase is followed by a 400 MB/s sequential read phase 530 which also lasts 10.5 ms. The read phase 530 suspends after the FIFO chip 230 becomes full or to accommodate any limits to down-stream throughput. For these extended periods of maximum rates of data arrival, this rough dynamic analysis implies that switching between phases may occur no more frequently than once every 10.5 ms. As a result, the overall RAID 150 throughput should only be compromised by a negligible amount. Note that during periods of slower, non-worst-case throughput, more frequent switching between phases can occur without penalty. With idle time negligible due to the low frequency of random access (0.1 ms between each 10.5 ms phase), almost all RAID 150 throughput is preserved, e.g., (10.5/(10.5+0.1)) or a very acceptable 99% of 400 or 396 MB/s. But that speed estimate is conservative with SSD rated at only 100 MB/s. Since the SSD are each likely to be somewhat faster than 100 MB/s, the actual RAID throughput may well exceed 400 MB/s.

In some embodiments, data flow #3 (of FIG. 2) may instead deliver the RAID output to the a stream buffer card FC F/O port, e.g., 210b, alone or possibly that port in conjunction with continued DMA output via the PCI Express interface 250. That FC F/O port is connected via duplex F/O cable to a compatible port on designated downstream hardware. In some embodiments, an alternate data flow affecting data flow #1 delivers the PET stream data 212, e.g., arriving on port 210a, out into the FC F/O port 210b as well as to the FIFO chip 230. For example, this modification to data flow #1 allows a secondary and independent data acquisition to occur on a secondary data acquisition system.

Figure 5:
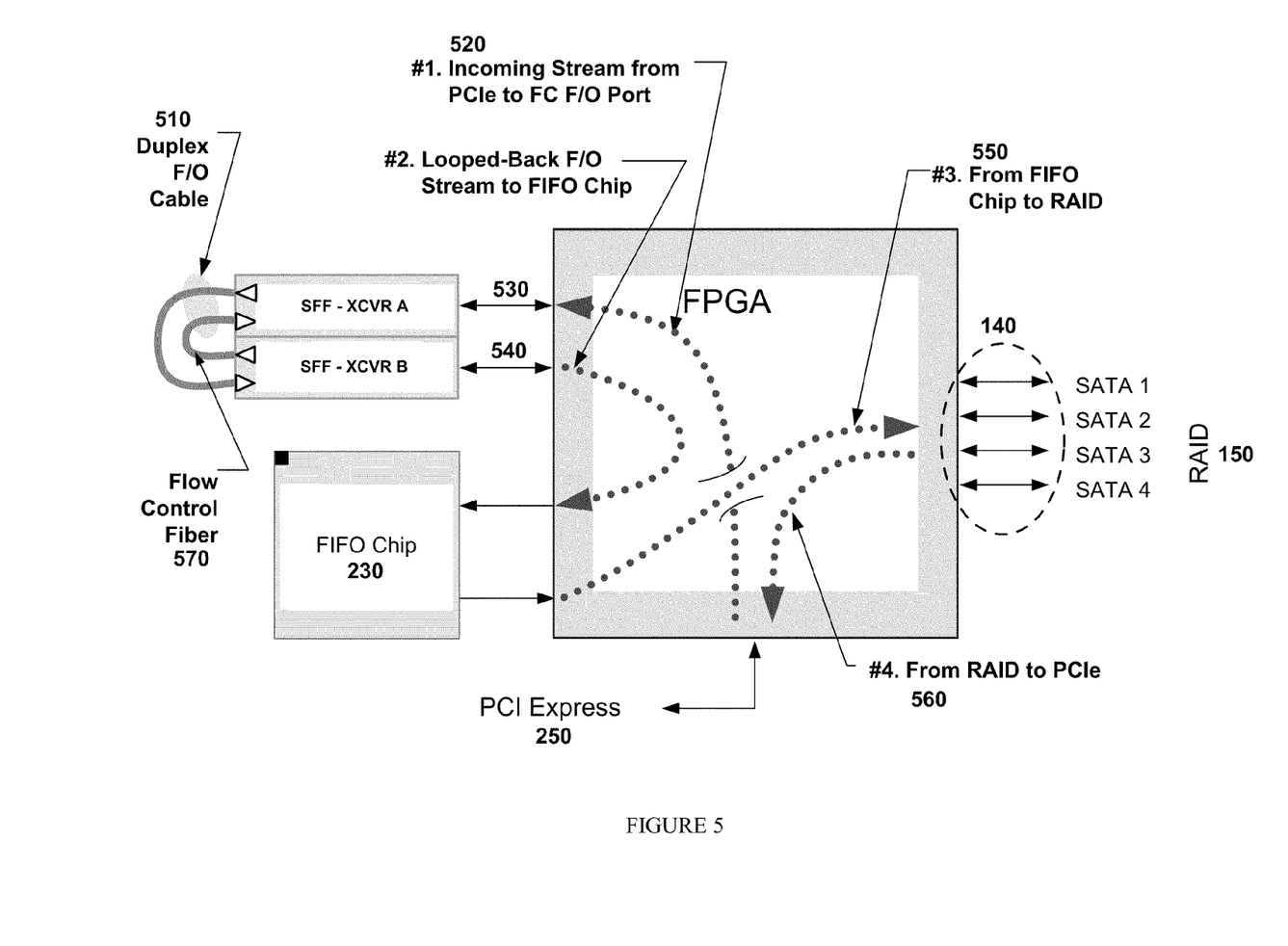
FIG. 5 illustrates a test configuration of a stream buffer.

FIG. 5 shows data flow for a self-test configuration for a stream buffer card. With the stream buffer card installed in a PC motherboard and with a duplex F/O loop-back cable 510 installed between the two FC F/O 210a, 210b ports, the card may be tested. Such a test can be valuable for both the test/development bench and for a quick check in the field, i.e., requiring only the duplex F/O cable 510 as special equipment. This data flow has four components. Dashed arrowhead lines are used to represent data flows. First 520, a predetermined list-mode data set is input to the card via PCI Express interface 250. This stream of data is output 530 by the FPGA 111 on one of the FC F/O ports. With the F/O loop-back cable 510 in place, this stream is returned 540 to the card on the other FC F/O port. The returning stream from the F/O loop-back is loaded into the FIFO chip 230. The FIFO chip 230 content is unloaded and written 550 sequentially to the RAID (not shown) via the SATA interface 140. The RAID content is read 560 via the SATA interface 140 and transferred, e.g., via PCI Express interface 250, e.g., to the PC motherboard. By having Windows Application Code comparing the "incoming data" in data flow 520 to the "outgoing data" in data flow 560 and showing equivalence, many aspects of stream buffer functionality can be checked. Note that one half of the duplex F/O link is used only for flow control 570. Here "flow control" means, for example, to communicate upstream either "OK-to-SEND" (such as by default sending only the "IDLE" Fibre Channel transmission character) or "SUSPEND" (such as by repeatedly sending the "NOS" Fibre Channel transmission character) signals depending on the fullness status (e.g., half full) of the FIFO chip 230. The FPGA 111 receives these flow control signals—signals that in this diagnostic example are also generated by this same FPGA 111—and responds to limit the rate of the incoming stream 520 from PCI Express interface 250, e.g., such that no data is lost. This flow control mechanism can prevent data loss for this diagnostic test from any of the following example causes: FIFO overflow, inadequate RAID bandwidth, inadequate rates of PCI Express interface output, etc. Such flow control also is useful for non-diagnostic PET applications in which the RAID output is retransmitted via the second, e.g., available, FC F/O port. See description of the alternate data flow for the RAID output discussed above. In such an example, the flow control signals pass fiber-optically upstream (into the stream buffer) to ensure that RAID output flowing fiber-optically downstream (out of the stream buffer) is not sent too rapidly.

On at least two other occasions, a "gating buffer" has been described for use in PET. In those cases, DRAM was configured to form a list-mode buffer of sufficient size to hold a few seconds of the PET stream. The goal was only to hold in memory the PET event stream generated during a single cardiac or respiratory cycle. This relatively small DRAM buffer (~1 GB or less) was primarily used for "bad-beat" (too short or too long) rejection of the cardiac cycle prior to histogramming. The stream buffer disclosed herein eliminates the need for a separate gating buffer.

The stream buffer offers at least one advantage over the traditional, smaller gating buffer. For cardiac gating in PET using the old-style gating buffer, on-line decisions for processing the PET event stream are usually restricted to details concerning each individual cardiac cycle. By contrast, with a stream buffer, on-line decisions related to downstream processing can be made across one or many cardiac cycles or even across many respiratory cycles. For example, presentations by Townsend et al., describe complex gating algorithms that were intended only for post-acquisition processing. With the stream buffer, the RAID (read) output can be delayed until a sufficient number of cardiac or respiratory cycles have been held and observed during the PET acquisition. Instead of just "bad beat" rejection, this stream buffer approach to on-line gating enables, for example, more complex handling of a very long series of "irregular beats."

To this end, the stream buffer FPGA can dynamically record (and provide to Windows application code via the PCI-E bus) real-time information about the still-growing file content. For example, Windows application code can receive from the FPGA in real-time a growing list of multi-faceted file pointers. These pointers indicate the locations within the stream buffer file for elapsed time marker (tag) packets, cardiac R-wave tag packets, respiratory inhalation-phase tag packets, general physiological waveform packets, bed position packets, etc. Once the Windows-resident code has real-time pointer information for the on-going PET data acquisition, the following parameters are readily calculated by the code for any portion of the acquisition, i.e., PET event rates, cardiac rates, respiratory rates, and their relationship one-to-the-other. Armed with this rich real-time data set, the Windows application code can support a variety of complex (e.g. dual-gating or even multiplex-gating) algorithms. Under control of the Windows application code, these algorithms, driven by this richer data set, can direct the stream buffer to read (and to even re-read) the RAID file content while the PET acquisition continues. By this method, various portions of the still-being-collected PET event stream file content can then be sent out for complex downstream processing as may be required or desired. Such effective on-line support across huge portions of the PET stream was never feasible with the old-style gating buffer architecture.

Figure 6:
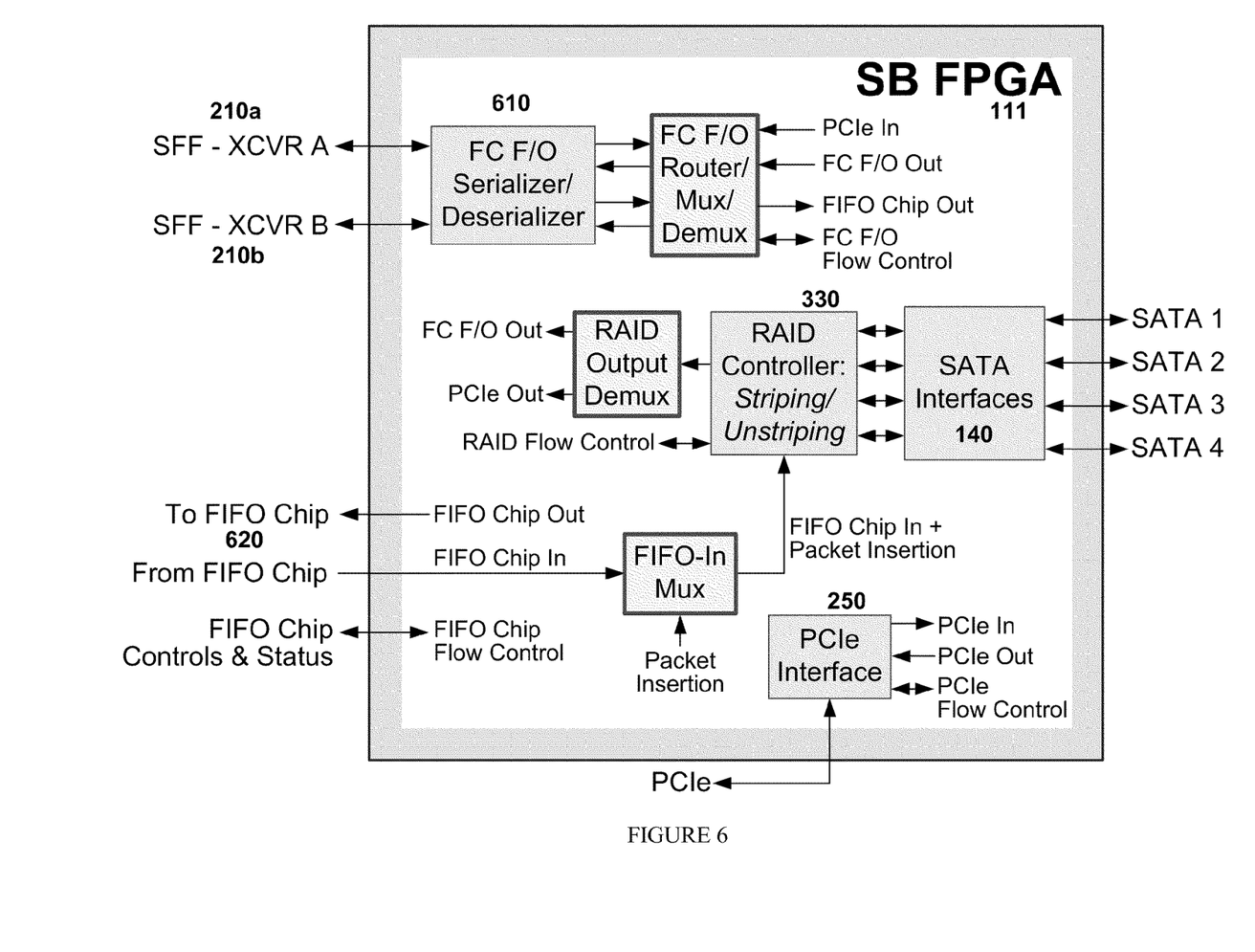
FIG. 6 is a block diagram of an exemplary FPGA used in embodiments of the technology.

FIG. 6 illustrates a block diagram of an FPGA 111 of the technology incorporating SATA interfaces 140, PC Express Interface 250, and logic 330. Raw data from the PET array is received via SFF-XCVR A F/O transceiver 210a using a dedicated FC F/O interface.

In conventional FC RAID with a conventional computer serving as the RAID host, the FC protocol includes the layer, FC-2—typically as part of a duplex FC link. This FC-2 layer supports an organizational complexity known as "frames." Each frame of data can be as large as ~2 k bytes. FC-2 frames have a payload of data, include "frame delimiters" and CRC error correction and support retransmission of corrupted data. In order to make use of the higher FC layers, e.g., FC-3 and FC-4, the system must also make use of FC-2. In some embodiments of the stream buffer (SB), the FC F/O input link from the PET detector array does not make use of or support FC-2. Instead, this stripped-down FC link only supports FC layers FC-0 and FC-1. In these embodiments, we have recognized the utility and economy of using only FC layers FC-0 and FC-1 for delivery of the PET coincidence event data streams. In contrast to conventional FC RAID, the incoming FC port on the stream buffer is simplex only, has no error correction, and no retransmission of corrupted data is possible.

The raw PET array data arrives at the FPGA 111 over such an interface via the transceiver 210a and is distributed via the serializer/deserializer 610 and router/mux/demux 620 to the FIFO chip 230 (not shown) via interface 620. The RAID controller 330 controls write striping of data from the FIFO chip 230 and reading/unstriping for output, e.g., through the PCI-Express interface 250.

Disclosed herein is a data acquisition architecture for clinical PET. In an enabling embodiment, a 4-channel SATA RAID 0, using a four 100 MB/s SSDs, is embedded within the data acquisition system. This embedded RAID serves as a stream buffer for the PET event stream. With this stream buffer, a shift in architectural focus occurs. Once the prospect of packet loss is largely eliminated due to the fast embedded RAID, the criticality of matching the real-time rebinning and real-time histogramming throughput to that of the maximum PET array output is greatly reduced if not wholly eliminated. A slightly slower down-stream processing from the embedded RAID, i.e., slower than the rate at which the PET detector array generates the data, does not result in loss of precious PET data. If the downstream processing that follows the RAID output (rebinning and histogramming) slows for brief periods or saturates during brief high-rate input bursts, the minor cost to the user may only be a few seconds delay in the delivery of the final projection data sets. The stream buffer also allows some cost reduction in delivered downstream hardware and a simpler, less-optimization-for-throughput Windows software development. In addition, the stream buffer can be leveraged to enhance on-line gated cardiac/respiratory) studies.

The technology can take the form of hardware, software or both hardware and software elements. In some embodiments, the technology is implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium (though propagation mediums in and of themselves as signal carriers are not included in the definition of physical computer-readable medium). Examples of a physical computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD. Both processors and program code for implementing each as aspect of the technology can be centralized or distributed (or a combination thereof) as known to those skilled in the art.

A data processing system suitable for storing program code and for executing program code will include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

The invention claimed is:

1. A positron emission tomography (PET) system, comprising:
   a PET array characterized by a data output rate,
   a PET data processing assembly characterized by a data input rate,
   a PET data acquisition assembly:
      in data communication with the PET array and the PET data processing assembly; and
      comprising:

a one-to-N channel write striping assembly in read communication with the PET array;
an N-to-one channel read unstriping assembly in write communication with the PET data processing assembly;
a plurality, N, of data storage elements, each data storage element:
  in read communication with one of the N channels of the write striping assembly, and
  in write communication with one of the N channels of the read unstriping assembly; and
a PET data acquisition control logic assembly:
  in control communication with the write striping assembly, the read unstriping assembly, and each of the N data storage elements, and
  operative to allocate write and read access to the N data storage elements.

2. The PET system of claim 1, wherein:
the control logic assembly allocates one half the data handling capacity of the data storage elements to read access and one half to write access.

3. The PET system of claim 1, wherein:
the control logic assembly allocates read access to the N data storage elements only on a condition that the N data storage elements be available to receive all input data from the PET array.

4. The PET system of claim 2:
wherein:
  the PET data acquisition assembly further comprises an input buffer in the data communications path between the PET array and the write striping assembly, and
  the control logic assembly further is in control communication with the input buffer; and
wherein the condition is determined dynamically at least in further part as a function of the capacity of the input buffer to preserve all PET input data supplied to the PET data acquisition assembly by the PET array during periods when the N data storage elements are unavailable as a write destination.

5. The PET system of claim 1, wherein:
the data communication between the PET array and the PET data acquisition assembly is Fibre Channel simplex implementing only the FC-0 and FC-1 layers.

6. The PET system of claim 1, wherein:
each of the plurality of N data storage elements is characterized by a data handling bandwidth equal to or greater than the (data output rate/N) plus the (data input rate/N).

7. The PET system of claim 1, wherein the control logic assembly, write striping assembly, and read unstriping assembly are implemented in a Field Programmable Gate Array (FPGA).

8. The PET system of claim 1, wherein the plurality of N data storage elements is a Redundant Array of Independent Disks (RAID).

9. The PET system of claim 8, wherein the RAID is a RAID 0.

10. The PET system of claim 1, wherein each of the plurality of N data storage elements is a solid state drive (SSD).

11. A sensor system, comprising:
a sensor array characterized by a data output rate,
a sensor data processing assembly characterized by a data input rate,
a sensor data acquisition assembly:
  in data communication with the sensor array and the sensor data processing assembly; and
  comprising:
    a one-to-N channel write striping assembly in read communication with the sensor array;
    an N-to-one channel read unstriping assembly in write communication with the sensor data processing assembly;
    a plurality, N, of data storage elements, each data storage element:
      in read communication with one of the N channels of the write striping assembly, and
      in write communication with one of the N channels of the read unstriping assembly; and
    a sensor data acquisition control logic assembly:
      in control communication with the write striping assembly, the read unstriping assembly, and each of the N data storage elements, and
      operative to allocate write and read access to the N data storage elements.

12. The sensor system of claim 11, wherein:
the control logic assembly allocates one half the data handling capacity of the data storage elements to read access and one half to write access.

13. The sensor system of claim 11, wherein:
the control logic assembly allocates read access to the N data storage elements only on a condition that the N data storage elements be available to receive all input data from the sensor array.

14. The sensor system of claim 12:
wherein:
  the sensor data acquisition assembly further comprises an input data buffer in the data communications path between the sensor array and the write striping assembly, and
  the control logic assembly further is in control communication with the input buffer; and
wherein the condition is determined dynamically at least in part as a function of the capacity of the input buffer to temporarily preserve all input data supplied to the data acquisition assembly during periods when such data cannot be written to the N data storage elements.

15. The sensor system of claim 11, wherein:
the data communication between the sensor array and the sensor data acquisition assembly is Fibre Channel simplex implementing only the FC-0 and FC-1 layers.

16. The sensor system of claim 11, wherein:
each of the plurality of N data storage elements is characterized by a data handling bandwidth equal to or greater than the (data output rate/N) plus the (data input rate/N).

17. The sensor system of claim 11, wherein the control logic assembly, write striping assembly, and read unstriping assembly are implemented in a Field Programmable Gate Array (FPGA).

18. The sensor system of claim 11, wherein the plurality of N data storage elements is a Redundant Array of Independent Disks (RAID).

19. The sensor system of claim 18, wherein the RAID is a RAID 0.

20. The sensor system of claim 11, wherein each of the plurality of N data storage elements is a solid state drive (SSD).

21. A data acquisition assembly comprising:
an input port;
an output port;
a one-to-N channel write striping assembly in data communication with the input port;
an N-to-one channel read unstriping assembly in data communication with the output port;

a plurality, N, of data storage elements, each data storage element:
    in read communication with one of the N channels of the write striping assembly, and
    in write communication with one of the N channels of the read unstriping assembly; and
a data acquisition control logic assembly:
    in control communication with the write striping assembly, the read unstriping assembly, and each of the N data storage elements, and
    operative to allocate write and read access to the N data storage elements.

22. The data acquisition assembly of claim 21, wherein:
the control logic assembly allocates one half the data handling capacity of the data storage elements to read access and one half to write access.

23. The data acquisition assembly of claim 21, wherein:
the control logic assembly allocates read access to the N data storage elements only on a condition that the N data storage elements be available to receive all data supplied to the input port.

24. The data acquisition assembly of claim 22:
wherein:
    the data acquisition assembly further comprises an input buffer in the data communications path between the input port and the write striping assembly, and
    the control logic assembly further is in control communication with the input buffer; and
wherein the condition is determined dynamically at least in part as a function of the capacity of the input buffer to temporarily preserve all input data supplied to the data acquisition assembly during periods when such data cannot be written to the N data storage elements.

25. The data acquisition assembly of claim 21, wherein:
the input port is a Fibre Channel simplex input port implementing only the FC-0 and FC-1 layers.

26. The data acquisition assembly of claim 21, wherein:
each of the plurality of N data storage elements is characterized by a data handling bandwidth equal to or greater than the (data output rate/N) plus the (data input rate/N).

27. The data acquisition assembly of claim 21, wherein the control logic assembly, write striping assembly, and read unstriping assembly are implemented in a Field Programmable Gate Array (FPGA).

28. The data acquisition assembly of claim 21, wherein the plurality of N data storage elements is a Redundant Array of Independent Disks (RAID).

29. The data acquisition assembly of claim 28, wherein the RAID is a RAID 0.

30. The data acquisition assembly of claim 21, wherein each of the plurality of N data storage elements is a solid state drive (SSD).

* * * * *